United States Patent [19]

Ascher

[11] Patent Number: 4,767,852

[45] Date of Patent: Aug. 30, 1988

[54] NEW PROCESS FOR PRODUCING CEPHALOSPORIN ANTIBIOTICS, AND NOVEL INTERMEDIATES FOR USE IN SUCH PROCESS AND THEIR PRODUCTION

[75] Inventor: Gerd Ascher, Wörgl, Austria

[73] Assignee: Biochemie, Tyrol, Austria

[21] Appl. No.: 932,759

[22] Filed: Nov. 19, 1986

Related U.S. Application Data

[63] Continuation of Ser. No. 427,199, Sep. 29, 1982, abandoned, which is a continuation of Ser. No. 248,609, Mar. 27, 1981, abandoned.

[30] Foreign Application Priority Data

Mar. 28, 1980 [AT] Austria .................. 1680/80

[51] Int. Cl.$^4$ .................. C07D 501/22; C07D 501/56
[52] U.S. Cl. .................. 540/222; 540/225; 540/227; 540/228; 548/170
[58] Field of Search .................. 540/227, 228, 222, 225

[56] References Cited

U.S. PATENT DOCUMENTS

| | | | |
|---|---|---|---|
| 3,737,423 | 6/1973 | Mukaiyama et al. | 530/340 |
| 3,830,794 | 8/1974 | Mukaiyama et al. | 530/333 |
| 4,220,761 | 9/1980 | Takaya et al. | 544/27 |
| 4,307,116 | 12/1981 | Farge et al. | 544/27 |
| 4,385,181 | 5/1983 | Farge et al. | 544/182 |
| 4,456,754 | 6/1984 | Murakami et al. | 544/27 |
| 4,477,448 | 10/1984 | Hamberger et al. | 544/27 |

FOREIGN PATENT DOCUMENTS

0002586 6/1979 European Pat. Off. .
0004570 10/1979 European Pat. Off. .

OTHER PUBLICATIONS

Zabicky, "The Chemistry of Amides", Interscience Publishers, 1970, p. 118.

*Primary Examiner*—Mary E. Ceperley
*Attorney, Agent, or Firm*—Gerald D. Sharkin; Robert S. Honor; Thomas O. McGovern

[57] ABSTRACT

Process for the production of known 2-oximinoacetamido-3-cephem-4-carboxylic derivatives comprising acylation of 7-amino-3-cephem-4-carboxylic acid derivatives with novel 2-oximinoacetic acid thio esters, as well as such thioesters and their production.

2 Claims, No Drawings

NEW PROCESS FOR PRODUCING CEPHALOSPORIN ANTIBIOTICS, AND NOVEL INTERMEDIATES FOR USE IN SUCH PROCESS AND THEIR PRODUCTION

This is a continuation of application Ser. No. 427,199, filed Sept. 29, 1982, now abandoned which in turn is a continuation of application Ser. No. 248,609, filed Mar. 27, 1981, now abandoned.

The invention relates to a new process for the production of syn-isomers of formula I,

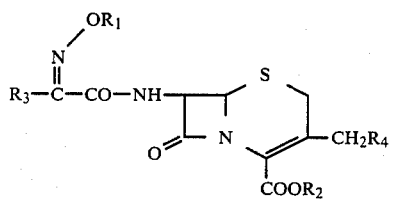

in which
- $R_1$ is hydrogen, alkyl, phenalkyl, carbalkoxyalkyl, acyl or carboxyalkyl,
- $R_2$ is hydrogen, pivaloyloxymethyl or a carboxy protecting group,
- $R_3$ is a 5-membered oxygen- or sulphur-containing heterocyclic ring, which may be substituted by amino or azido, and
- $R_4$ is hydrogen, acetoxy, carbamoyloxy of —S—Y, in which Y is a heterocyclic ring which may be substituted.

The compounds of formula I represent a known class of valuable cephalosporin antibiotics disclosed for example in W. German DOS Nos. 2,223,375; 2,556,736; 2,702,501; 2,707,565; 2,715,385; 2,992,036; as well as numerous other patent and other publications. This class of antibiotics is characterised by the presence of an oximino group in the 7-acylamido side-chain attached to the cephalosporin nucleus. It is known that this oximino group may have the syn of anti configuration but that the syn isomers are preferred.

The heterocyclic ring in $R_3$ contains, as indicated, one or more oxygen and/or sulphur atoms as heteroatom(s). It may, however, additionally contain one or more nitrogen hetero atoms. Suitable heterocyclic rings include furyl, thienyl, thiazolyl, thiadiazolyl, oxazolyl and oxadiazolyl. The heterocyclic ring may as indicated be unsubstituted or substituted by amino or azido, preferably amino. Preferably the heterocyclic ring of $R_3$ is thiazolyl and this is preferably substituted by amino.

A particular preferred group of syn-isomers is that of formula Ia,

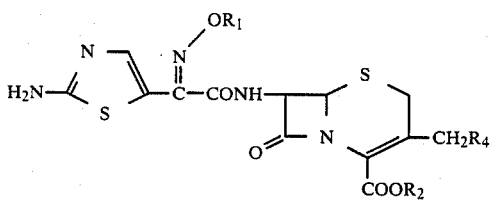

in which $R_1$, $R_2$ and $R_4$ are as defined above.

In these structures, the radical $R_4$ can be hydrogen. It may also be carbamoyloxy. It is, however, preferably, acetoxy or —S—Y. Suitable heterocyclic groups which Y may represent are well-known, for example from the numerous publications referred to above. Preferred heterocyclic rings include thiadiazolyl, diazolyl, triazolyl, tetrazolyl, thiazolyl, thiatriazolyl, oxazolyl, oxadiazolyl, triazolylpyridyl, purinyl, pyridyl, pyrimidinyl, pyridazinyl, pyrazolyl or triazinyl. These heterocyclic rings may be unsubstituted or substituted, for example up to three times. Suitable substituents include $C_{1-4}$alkyl, $C_{1-4}$alkoxy, halogen, trihalo-$C_{1-4}$ alkyl, hydroxy, oxo, mercapto, amino, carboxyl, carbamoyl, di-($C_{1-4}$)alkylamino, carboxymethyl, carbamoylmethyl, sulphomethyl and methoxycarbonylamino. Heterocyclic moieties indicated in the prior art to be particularly preferred include tetrazolyl, in particular 1-methyl-1H-tetrazol-5-yl, and triazinyl, in particular 1,2,5,6-tetrahydro-2-methyl-5,6-dioxo-as-triazin-3-yl, 2,5-dihydro-6-hydroxy-2-methyl-5-oxo-as-triazin-3-yl or 1,4,5,6-tetrahydro-4-methyl-5,6-dioxo-as-triazin-3-yl. Preferably $R_4$ is acetoxy, 1-methyl-1H-tetrazol-5-yl, or 2,5-dihydro-6-hydroxy-2-methyl-5-oxo-as-triazin-3-yl.

In these structures, $R_1$ may be hydrogen. It may also be $C_{1-4}$alkyl preferably $C_{1-2}$alkyl, in particular methyl. Suitable phenalkyl groups include phen-$C_{1-4}$-alkyl, particularly benzyl. $R_1$ may also be carbalkoxyalkyl, for example carb($C_{1-2}$)alkoxy($C_{1-4}$)alkyl, in particular carb($C_{1-4}$)alkoxymethyl, e.g. carbethoxymethyl. Suitable acyl radicals include $C_{2-5}$alkanoyl or, $C_{1-4}$alkoxycarbonyl. $R_1$ may also be carboxyalkyl, in particular carboxy-$C_{1-4}$alkyl, e.g. carboxymethyl.

As is well known in the cephalosporin field, the compounds may be in the form of free acids ($R_2$=H) or of salts, for example alkali or alkaline earth metal salts, preferably alkali metal salts, such as sodium salts. Alternatively, the compounds may be in the form of esters, e.g. the pivaloyloxymethyl ester. ($R_2$=pivaloyloxymethyl). Other carboxy protecting groups which $R_2$ may represent are well-known and include acetoxymethyl, 1-acetoxyethyl, 1-ethoxycarbonyloxyethyl, 5-indanoyl or, preferably, hexanoylmethyl, phthalidyl, carbethoxymethoxymethyl or 3-carbethoxy-1-acetonyl.

Particularly preferred compounds are syn-isomers having the formula Ib,

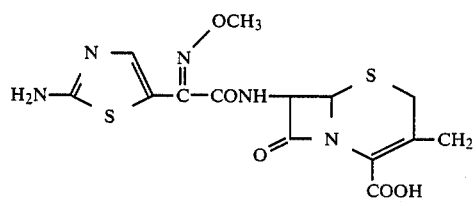

in which $R_4'$ is acetoxy, 1-methyl-1H-tetrazol-5-yl, or 2,5-dihydro-6-hydroxy-2-methyl-5-oxo-as-triazin-3-yl, and salts thereof.

The compounds of formula Ib are the products known as Cefotaxim ($R_4'$=acetoxy), SCE-1365 ($R_4'$=1-methyl-1H-tetrazol-5-yl) and Ceftriaxone ($R_o$13-9904) ($R_4'$=2,5-dihydro-6-hydroxy-2-methyl-5-oxo-as-triazin-3-yl), in the form of sodium salts (Cefotaxim and SCE-1365) or the disodium salt (Ceftriaxone).

As indicated, the compounds of formula I are generally known, and various methods for their production have been proposed. One such method involves acylation of the corresponding 7-aminocephalosporanic acid derivative, which may be protected, with a reactive derivative of the acid of formula A,

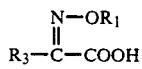

in which $R_1$ and $R_3$ are as defined above.

The various reactive derivatives that have been proposed include activated esters. For the production of the syn-isomers of formula I the reactive derivatives of the acid of formula A should also be in syn-isomeric form in as high a purity as possible, and the syn-configuration should as far as possible be unaffected by the subsequent steps, in particular the acylation step. Various reactive derivatives that have previously been proposed, in particular activated esters, suffer from the disadvantage that the syn-configuration is somewhat unstable during production or use thus leading to increased formation of the anti-isomer and consequential reduction of the yields of the desired syn-isomers.

A further difficulty that arises in the production of the preferred compounds of formula Ia is that in practice it is essential to protect the amino substituent in the thiazolyl ring of the side-chain prior to the acylation step. Otherwise competing reactions can occur leading to greatly reduced yields of the final products. The introduction, however, of suitable protecting groups prior to the acylation step, and their subsequent removal is in general accompanied by reduced yield and purity of the desired final product and not insubstantial additional reaction time, energy, effort and cost.

The present invention provides a method by which the desired syn-isomers may be obtained in high purity and yield; in particular, the syn-isomers of formula Ia may be obtained in high purity and yield without the necessity to protect the amino substituent in the thiazolyl ring of the side-chain.

More particularly, the present invention provides a process for the production of syn-isomers of formula I and salts thereof, comprising reacting a syn-isomer of formula II,

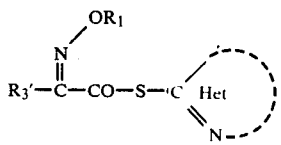

in which
$R_1$ is as defined above,
$R_3'$ is a 5-membered oxygen- or sulphur-containing heterocyclic ring, which may be substituted by amino, protected amino, or azido, and

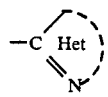

represents a 5- or 6-membered heterocyclic ring, which may contain in addition to the nitrogen atom, one or two further hetero atoms, selected from oxygen, nitrogen and sulphur, and which may be substituted or fused to a benzene ring which may itself be substituted,
with a compound of formula III.

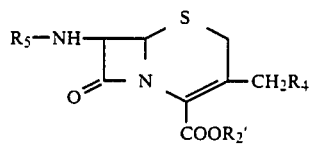

in which
$R_2$ and $R_4$ are as defined above, and
$R_5$ is hydrogen or an amino protecting group,
where required, disprotecting the resulting product, and, where required, converting a resulting product in which $R_2$ is hydrogen into a salt thereof or vice versa.

The process is suitably carried out in an inert organic solvent, such as a chlorinated hydrocarbon, e.g. methylene dichloride, or an ether, e.g. ethyl acetate, or in a mixture of such solvents with water. The reaction temperature is suitably from $-40°$ to $+60°$ C., in particular $-15°$ to $+25°$ C., espcially $0°$ to $20°$ C., and the reaction time may typically vary from ½ to 48 hours. The reactants of formula II or III may conveniently be employed in stoichiometric quantities. Alternatively, an excess of up to 25% of the compound of formula II is conveniently employed.

As indicated, the production of compounds in which $R_2$ is hydrogen (as well as salts thereof), the carboxylic acid group in the starting material of formula II, is conveniently protected. Suitable protecting groups are well known and include not only those referred to above as possible significances for $R_2$, but also silyl ester protecting groups, in particular the trimethylsilyl protecting groups, which may for example be introduced by reaction of the free acid with N,O-bis-trimethylsilylacetamide.

The 7-amino group of the starting material of formula III may, as indicated, also be protected. Again, suitable protecting groups are well-known and include for example the trimethylsilyl group, which may for example be introduced simultaneously when protecting the carboxylic acid group.

When $R_3$ in the desired product contains an amino substituent in the heterocyclic ring, the corresponding starting material of formula II may have this amino substituent in free or in protected form. As discussed, in general protection is not necessary. If protection is nevertheless desired, this may be accomplished in conventional manner, suitable protecting groups being well-known.

After reaction of the compounds of formula II and III, any subsequent disprotection steps may be effected in conventional manner. Likewise, interconversion of the free acid ($R_2=H$) and salts thereof may be accomplished in well-known manner.

The resulting products may be isolated and purified using conventional techniques.

The process of the invention thus employs as reactive derivatives of the acid of formula A, heterocyclic thioesters. It has been surprisingly found that these esters may be prepared and employed with virtually complete control of the geometry of the —C=N— syn-configuration. Furthermore, it has surprisingly been found that when there is an amino group in the heterocyclic ring of these esters, the esters are not self-reacting. Accordingly, protection of this amino group in the subsequent acylation is not essential (although of course not ruled out if for any reason desired).

The syn-isomers of formula II are novel and also form part of the present invention. The nature of the

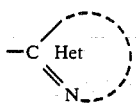

ring therein is not critical, the preferred compounds being determined by such factors as ease of formation and availability of starting materials. Preferably, however, this signifies 2-pyridyl, or, especially, 2-benzthiazolyl. The preferred compounds of formula II correspond to the preferred end products, namely syn isomers of formula IIa and IIb,

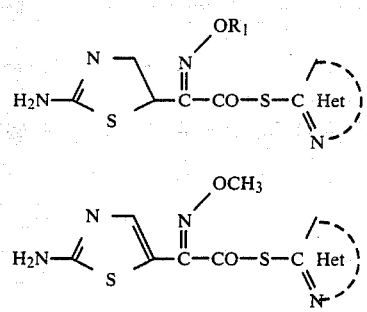

in which $R_1$ and

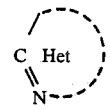

are as defined above.

In accordance with the invention, the syn-isomers of formula II may be prepared by esterification of a syn-isomer of formula IV,

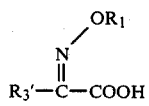

in which $R_1$ and $R_3'$ are as defined above.

The esterification may for example be accomplished by reaction with a compound of formula V,

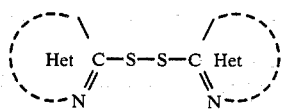

in which the two groups

are the same and are as defined above.

The reaction is suitably effected in the presence of a tri-(lower alkyl)- or tri(aryl)phosphine or phosphite, in particular triphenylphosphine. The reaction temperature may for example be from $-30°$ to $+50°$ C., in particular $-20°$ to $+25°$ C., preferably $-5°$ to $+5°$ C. The reaction is suitably effected in an inert, non-hydroxy-containing-, organic solvent, for example a chlorinated hydrocarbon, such as methylene chloride. Where a compound of formula II in which $R_3$ is a protected-amino-substituted heterocycle is desired, the amino protecting group may of course be introduced prior to or subsequent to the esterification reaction.

The syn-isomers of formula I are as indicated in general known antibiotics. In particular they are useful as antibacterial agents as indicated in vitro in the series dilution test, at a concentration for example of 0.01 to 50 µg/ml, and in vivo in the mouse at a dosage of for example from 0.1 to 100 mg/kg of animal body weight, against a wide variety of strains, such as *Staphylococcus aureus, Streptococcus pyogenes, Streptococcus faecalis, E. coli, Proteus vulgarix, Proteus mirabilis, Proteus morganii, Shigella dysenteria, Shigella sonnei, Shigella flexneri, Alcaligenes faecalis, Klebsiella aerogenes, Klebsiella penumoniae, Serrata marcescens, Salmonella Heidelberg, Salmonella typhinurium, Salmonella enteritidis* and *Neuseria gonorrhoae*.

The compounds are therefore useful as bacterially active antibiotics. For this usage, the dosage will of course vary depending on the compound employed, mode of administration and treatment desired. However, in general, satisfactory results are obtained when administered at a daily dosage of from 10 to 100 mg/kg of animal body weight, conveniently given in divided dosages 2 to 4 times daily, or in sustained release form. For the larger mammals, the total daily dosage is in the range of 1 to 6 g and dosage forms suitable for oral administration comprise from about 0.25 to about 3 g of the compound admixed with a solid or liquid pharmaceutical carrier or diluent.

The compounds in which $R_2$ is hydrogen may be employed in free acid form or in the form of their physiologically acceptable salts, which salt forms have the same order of activity as the free acid forms. Suitable salt forms include alkali metal and alkaline earth metal salt forms, in particular alkali metal, such as sodium salt forms. The compounds may be admixed with conventional pharmaceutically acceptable diluents and carriers and optionally other excipients and administered in such forms as capsules or injectable preparations.

The following Examples in which all temperatures are in degrees Centigrade, illustrate the invention.

EXAMPLE 1

7-{[2-(2-Aminothiazol-4-yl)-2-syn-methoximino]acetamido}cephalosporanic acid [Cefotaxim]

2.72 g of 7-Aminocephalosporanic acid are suspended in 50 ml of methylene dichloride. 3.5 ml of N,O-bis-(trimethylsilyl)acetamide are added and the mixture is stirred at room temperature until a clear solution is obtained. 3.5 g of 2-(2-aminothiazol-4-yl)-2-syn-methoximino acetic acid 2-benzthiazolyl thioester are added and the mixture is stirred for 15 hours at room temperature. The solution is then extracted with 2 g of KHCO3 and 40 ml of water and the phases are separated. The aqueous phase is extracted with a mixture of ethyl acetate/n-butanol (8/2) at pH 2 and before phase separation, the aqueous phase is saturated with (NH4)2SO4. The organic phase is washed twice with 100 ml of NaCl solution and evaporated to dryness. The crystalline residue is shaken with 100 ml of diethyl ether, filtered and washed with ether. The title product is obtained.

M.P. 205° (decomp.). Yield 4.2 g; 92% of theory based on pure syn isomer.

EXAMPLE 2

7-[2-(2-Aminothiazol-4-yl)-2-syn-methoximino]acetamido cephalosporanic acid [Cefotaxim]

2.72 g of 7-Aminocephalosporanic acid are suspended in 40 ml of methylene dichloride and 2.75 ml of N,O-bis-(trimethylsilyl)acetamide are added, dropwise. The mixture is stirred until a clear solution is obtained. 2.9 g of 2-(2-aminothiazol-4-yl)-2-syn-methaminoacetic acid 2-pyridyl thioester are added, the mixture is cooled to 10° and stirred at this temperature for 24 hours. 2 g of KHCO$_3$ in 40 ml of water are added and the mixture is stirred for 30 minutes and the aqueous phase is separated. This is layered with a mixture of n-butanol/ethyl acetate and the pH of the mixture is adjusted to 2. The organic phase is evaporated in vacuo and the residue is mixed with ether. The precipitated crystalline heading compound is filtered off, washed with ether and dried. M.P. 205° (decomp.). Yield 4.1 g; 90% of theory based on pure syn isomer.

EXAMPLE 3

7-{[2-(2-Aminothiazol-4-yl)-2-syn-methoximino]acetamido}3-{[(2,5-dihydro-6-hydroxy-2-methyl-5-oxo-a,s-triazin-3-yl)thio]methyl}-3-cephem-4-carboxylic acid Ceftriaxon 3.71 g of 7-Amino-3-(2,5-dihydro-2-methyl-6-hydroxy-5-oxo-a,s-triazin-3-yl)thiomethyl-3-cephem-4-carboxylic acid are suspended in 50 ml of dry methylene chloride under an inert gas atmosphere. 8 ml of N,O-bis-(trimethylsilyl)acetamide are added, with stirring, and the mixture is stirred for 30 minutes when a clear solution is formed which is then cooled to +15° C. 4 g of 2-(2-aminothiazol-4-yl)-2-syn-methoximino acetic acid 2-benzthiazolyl thioester are added and the mixture is stirred for 5 hours at 15° to 20°, whereupon a clear solution is formed. The mixture is then cooled to 0° C. and poured into a solution of 3 ml of methanol in 120 ml of acetonitrile, pre-cooled to 0°. From the resulting initially clear solution, a light precipitate is formed on further stirring at 0° to 5° and this is filtered off and washed with acetonitrile. After drying in vacuum at 50° C., 4.7 g (85%) of substantially pure title compound are obtained, in the form of the free acid, m.p.>120° C. (decomp.).

EXAMPLE 4

7{[2-Aminothiazol-4-yl)-2-syn-methoximino]acetamido}-3-(1-methyl-1H-tetrazol-5-yl)thiomethyl-3-cephem-4-carboxylic acid [SCE 1365]

In manner analogous to that of any one of Examples 1 to 3, employing appropriate starting materials in approximately equivalent amounts, the heading compound may be obtained.

EXAMPLE 5

2-(2-Aminothiazol-4-yl)-2-syn-methoximinoacetic acid 2-pyridyl thioester [Compound II]

26 g of triphenylphosphine are dissolved in 130 ml of methylene dichloride and 22 g of 2,2-dithiopyridine are added. The mixture is stirred at room temperature for 15 minutes and then cooled to 0°. 10 g of finely powdered 2-(2-aminothiazol-4-yl)-2-syn-methoximinoacetic acid are then added in portions over 1 hour. The mixture is seeded and cooled for 3 hours at 0°, whereby the heading compound crystallises out. This is filtered and washed with cold methylene chloride; m.p. 112°; yield 16.4 g—98% of theory based on pure syn isomer.

EXAMPLE 6

2-(2-Aminothiazol-4-yl)-2-syn-methoximino acetic acid 2-benzothiazolyl thioester [Compound II]

3.93 g of Triphenylphosphine and 5 g of bis[benzthiazolyl-(2)]disulphide are suspended in 50 ml of methylene dichloride and the suspension is stirred for 30 minutes at room temperature. After cooling to 0°, 2 g of 2-(2-aminothiazol-4-yl)-2-syn-methoximinoacetic acid are added and the mixture is stirred for 3 to 4 hours at 0°. The insolubles are filtered off and washed with a little cold methylene dichloride. The solid is suspended in 25 ml of ethyl acetate and the suspension is stirred for 30 minutes at 0°, filtered and washed with ethyl acetate to obtain the heading compound, m.p. 128°-130° (from tetrahydrofuran/methylene dichloride).

What is claimed is:

1. In the process for the production of a syn-isomer of the formula Ia,

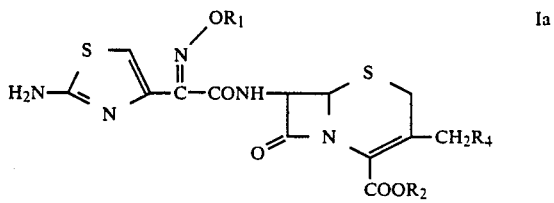

in which
R$_1$ is hydrogen, alkyl, phenalkyl, carbalkoxyalkyl, acyl or carboxyalkyl,
R$_2$ is hydrogen, pivaloyloxymethyl or a carboxy protecting group, and
R$_4$ is hydrogen, acetoxy, carbamoyloxy or —S—Y, in which Y is a heterocyclic ring which may be substituted;

or a pharmaceutically acceptable salt form thereof, which process comprises acylating a compound of formula III,

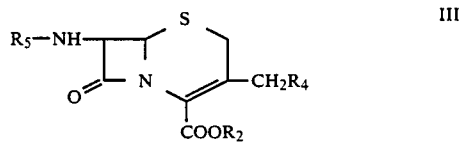

in which
R$_2$ and R$_4$ are as defined above, and
R$_5$ is hydrogen or an amino protecting group, with a reactive derivative of the acid of the formula,

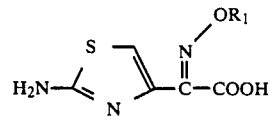

wherein R$_1$ is defined above; and effecting any subsequent disprotecting steps and interconversion of the free acid in which R$_2$ is hydrogen and salts thereof required to obtain a syn-isomer of formula Ia or a pharmaceutically acceptable salt form thereof, the improvement which comprises employing as said reactive derivative a syn-isomer of the formula IIa:

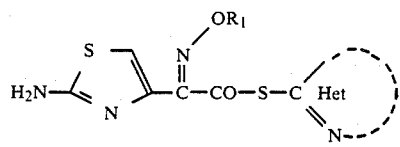
where R₁ is as defined above, and
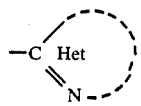
is 2-benzthiazolyl.
2. A process according to claim 1 for the production of syn-isomers of the formula Ib,
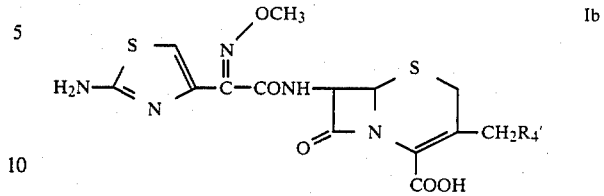
in which $R_4'$ is acetoxy or —S—Y in which Y is 1-methyl-1H-tetrazol-5-yl or 2,5-dihydro-6-hydroxy-2-methyl-5-oxo-as-triazin-3-yl, or a pharmaceutically acceptable salt form thereof.
* * * * *